United States Patent
Sendai

(10) Patent No.: US 8,192,361 B2
(45) Date of Patent: Jun. 5, 2012

(54) MULTI-MODALITY MAMMOGRAPHY IMAGING DEVICE FOR IMPROVED IMAGING CONDITIONS

(75) Inventor: Tomonari Sendai, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1108 days.

(21) Appl. No.: 11/958,666

(22) Filed: Dec. 18, 2007

(65) Prior Publication Data

US 2009/0118614 A1    May 7, 2009

(30) Foreign Application Priority Data

Dec. 27, 2006 (JP) ................................. 2006-351634

(51) Int. Cl.
*A61B 8/00* (2006.01)
(52) U.S. Cl. ........ 600/437; 600/407; 600/425; 600/443; 378/37; 378/62; 378/63
(58) Field of Classification Search .................. 600/425, 600/437, 443; 378/37, 62, 63
See application file for complete search history.

(56) References Cited

U.S. PATENT DOCUMENTS

| | | | |
|---|---|---|---|
| 5,479,927 A | | 1/1996 | Shmulewitz |
| 6,846,289 B2 * | | 1/2005 | Besson et al. ............... 600/437 |
| 2002/0094113 A1 * | | 7/2002 | Shinbata ....................... 382/128 |
| 2003/0007598 A1 * | | 1/2003 | Wang et al. ..................... 378/37 |
| 2007/0167782 A1 * | | 7/2007 | Callahan et al. ............. 600/443 |
| 2008/0242979 A1 * | | 10/2008 | Fisher et al. ................. 600/427 |

FOREIGN PATENT DOCUMENTS

| | | |
|---|---|---|
| JP | 05-183817 A | 7/1993 |
| JP | 2000060832 A | 2/2000 |
| JP | 2001-187044 A | 7/2001 |
| JP | 2003-230558 A | 8/2003 |
| JP | 2003-275196 A | 9/2003 |
| JP | 2006-051198 A | 2/2006 |
| JP | 2006-305337 A | 11/2006 |

OTHER PUBLICATIONS

Japanese Office Action dated Jul. 5, 2011, corresponding to Japanese Patent Application No. 2006-351634.
Japanese Office Action corresponding to Japanese Patent Applicaiton 2006-351634, dated Feb. 8, 2012.

* cited by examiner

*Primary Examiner* — James Kish
(74) *Attorney, Agent, or Firm* — Sughrue Mion, PLLC

(57) ABSTRACT

In a medical imaging system including plural imaging section, detection accuracy and examination efficiency for breast cancer are improved by setting appropriate imaging condition. The system includes: a first imaging section for imaging an object to be inspected by using one of radiation, ultrasonic waves, nuclear magnetic resonance, positron, infrared light and fluorescence to generate a medical image; a second imaging section for imaging the object by using another one of radiation, ultrasonic waves, nuclear magnetic resonance, positron, infrared light and fluorescence to generate a medical image; and an imaging condition setting section for setting imaging condition in the second imaging section based on the medical image generated by the first imaging section.

8 Claims, 13 Drawing Sheets

FIG.6

| DILATION | $(f \oplus G^S)(i) = \max\{f(i-m), \cdots, f(i), \cdots, f(i+m)\}$ |
|---|---|
| EROSION | $(f \ominus G^S)(i) = \min\{f(i-m), \cdots, f(i), \cdots, f(i+m)\}$ |
| OPENING | $f_g = (f \ominus g^S) \oplus g$ |
| CLOSING | $f^g = (f \oplus g^S) \ominus g$ |

| f7 | f6 | f5 | f4 | f3 |
|----|----|----|----|----|
| f8 |    |    |    | f2 |
| f9 |    | xj |    | f1 |
| f10|    |    |    | f16|
| f11| f12| f13| f14| f15|

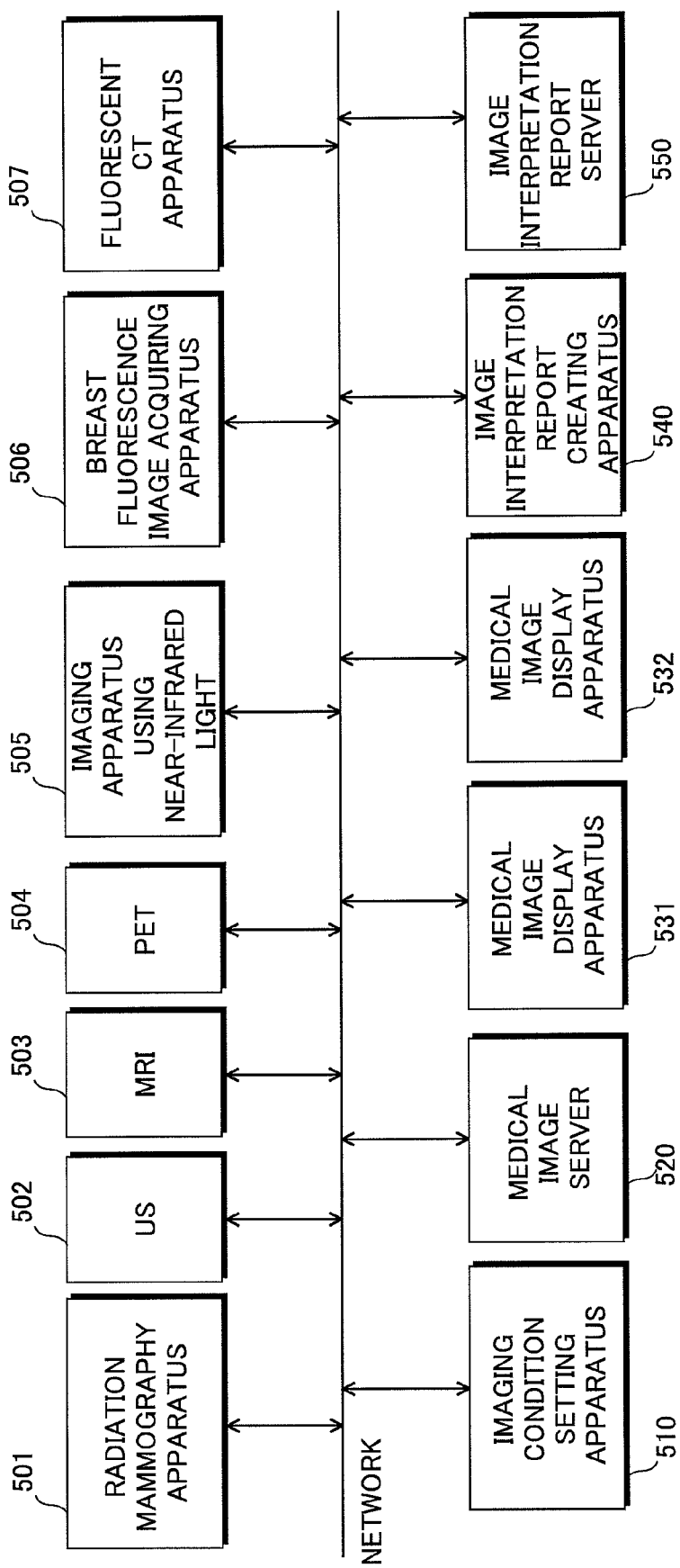

MULTI-MODALITY MAMMOGRAPHY IMAGING DEVICE FOR IMPROVED IMAGING CONDITIONS

The present application claims priority from Japanese Patent Application No. 2006-351634 filed on Dec. 27, 2006, the contents of which are incorporated herein by reference in their entirety.

BACKGROUND OF THE INVENTION

1. Field of the Invention

The present invention relates to medical imaging system and method for generating medical images to be used for medical diagnoses, and specifically, relates to medical imaging system and method employing plural imaging apparatus such as a radiation mammography apparatus and an ultrasonic imaging apparatus.

2. Description of a Related Art

Recent years, breast cancer patients have been increasing not only in Europe and the United States but also in Japan. However, even when a breast has a cancer, early treatment can cure the breast cancer relatively easily without the need for breast amputation in many cases. Accordingly, apparatuses and systems for early detection of breast cancer are desired.

When a breast has a cancer, a tumor mass and calcification are produced in the breast. Therefore, finding the lesion parts as earlier in minimal size as possible leads to early detection of breast cancer. Currently, the mainstream technologies for the purpose are X-ray mammography examination and ultrasonic imaging examination. Here, X-ray mammography refers to a method of making medical diagnoses based on X-ray images obtained by using an X-ray imaging apparatus for breast (X-ray mammography apparatus). On the other hand, in ultrasonic imaging examination, ultrasonic images are generated based on reception data obtained by transmitting ultrasonic waves to an object to be inspected and receiving ultrasonic echoes reflected within the object, and the presence or absence of lesion is determined based on the ultrasonic images. The X-ray mammography and ultrasonic imaging have the following features, respectively.

X-ray mammography is suitable for exposing calcification as one of early symptoms of the cancer, and enables detection with high sensitivity and high resolving power. Further, in the case where mammary gland tissues have become atrophied and replaced with fat (so-called "fat breast") as is the case of postmenopausal women, more information can be obtained by X-ray mammography. However, the X-ray imaging has a disadvantage that detection capability of specific natures of tissues (tissue properties) is low. Further, in an X-ray image, mammary glands are expressed in homogeneous soft tissue density, and thus, the detection of tumor mass is difficult in the case where mammary glands have developed (so-called, "dense breast") as is the case of adolescent to premenopausal women. Furthermore, in X-ray mammography, only two-dimensional images in which the object as a solid is projected on a plane can be obtained. On this account, even when a tumor mass is found, it is difficult to take a sample for determination of benign or malignant lesion.

On the other hand, in ultrasonic imaging, specific natures of tissues (e.g., the difference between a cystic tumor and a solid matter) can be detected, and also a lobular cancer can be detected. Further, real time observation of images and three-dimensional image generation are possible. However, ultrasonic imaging examination often depends on the skill of an examiner (an operator such as a doctor) in accuracy and low in reproducibility. Further, it is difficult to observe minute calcification in an ultrasonic image.

As described above, X-ray mammography examination and ultrasonic imaging examination have both merits and demerits, and it is desirable that both examinations are performed for reliable detection of breast cancer.

As a related technology, U.S. Pat. No. 5,479,927 discloses a method and apparatus for generating ultrasonic images of the internal structure of breast tissue which images are in geometric registration with a mammogram by the combination of X-ray mammography and ultrasonic imaging. The apparatus includes a radiolucent (X-ray lucent) and sonolucent compression plate, and a gantry driven ultrasound transducer or a phased array ultrasonic transducer. Further, in the method, a mammogram and a plurality of corresponding ultrasound images are generated without moving the breast between the mammogram exposure and the ultrasound imaging.

However, in U.S. Pat. No. 5,479,927, by the combination of an X-ray mammography apparatus and an ultrasonic imaging apparatus, only two kinds of examination images correlated with respect to positions of the object or their synthesized images can be generated, but no effort is made to mutually utilize information obtained by the respective examination apparatuses.

Further, in either X-ray mammography or ultrasonic imaging, image statuses to be generated largely differ depending on imaging condition. However, appropriate imaging condition varies according to object statuses, and thus, it is often difficult to set appropriate imaging condition depending on skills of examiners.

SUMMARY OF THE INVENTION

The present invention has been achieved in view of the above-mentioned problems. A purpose of the present invention is, in a medical imaging system with combination of plural imaging apparatuses such as a radiation mammography and an ultrasonic imaging apparatus, to set appropriate imaging condition by taking advantage of characteristics of examination using the respective imaging apparatuses.

In order to accomplish the above-mentioned purpose, a medical imaging system according to one aspect of the present invention is a system including plural imaging means, and the system includes: first imaging means for imaging an object to be inspected by using one of radiation, ultrasonic waves, nuclear magnetic resonance, positron, infrared light and fluorescence to generate a medical image; second imaging means for imaging the object by using another one of radiation, ultrasonic waves, nuclear magnetic resonance, positron, infrared light and fluorescence to generate a medical image; and imaging condition setting means for setting imaging condition in the second imaging means based on the medical image generated by the first imaging means.

Further, a medical imaging method according to one aspect of the present invention is a method of generating medical images by employing plural imaging means, and includes the steps of: (a) generating a first medical image by employing first imaging means for imaging an object to be inspected by using one of radiation, ultrasonic waves, nuclear magnetic resonance, positron, infrared light and fluorescence; (b) generating a second medical image by employing second imaging means for imaging the object by using another one of radiation, ultrasonic waves, nuclear magnetic resonance, positron, infrared light and fluorescence; and (c) setting imaging condition in the second imaging means based on the first medical image prior to step (b).

According to one aspect of the present invention, on the basis of the information obtained by performing an examination using the first imaging means (e.g., one of the X-ray mammography apparatus and the ultrasonic imaging apparatus), imaging condition in an examination using the second imaging means (e.g., the other of the X-ray mammography apparatus and the ultrasonic imaging apparatus) are automatically set, and thereby, medical images imaged under appropriate imaging condition according to the characteristics of the respective imaging means and the object status can be obtained. Therefore, for example, in breast cancer screening using both the X-ray mammography apparatus and the ultrasonic imaging apparatus, the detection accuracy of the lesion part such as calcification or tumor mass can be improved and the examination efficiency can be improved regardless of the skills of examiners.

BRIEF DESCRIPTION OF THE DRAWINGS

FIG. 6 shows basic operations of mathematical morphology;

FIG. 14 is a block diagram showing a configuration of a medical imaging system according to the second embodiment of the present invention.

DESCRIPTION OF THE PREFERRED EMBODIMENTS

Hereinafter, preferred embodiments of the present invention will be explained in detail with reference to the drawings. The same reference numbers are assigned to the same component elements and the description thereof will be omitted.

Figure 1:
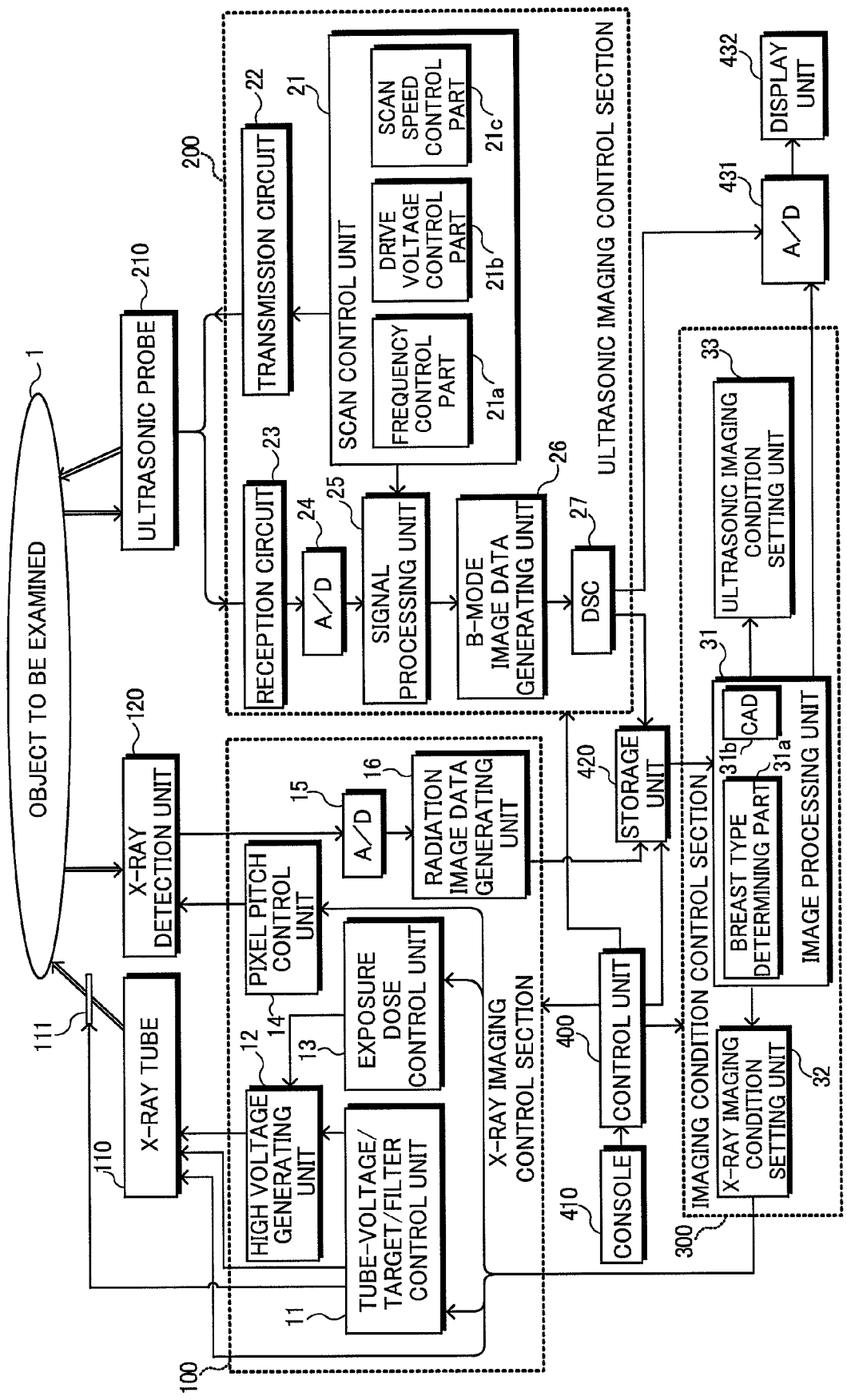
FIG. 1 is a block diagram showing a configuration of a medical imaging system according to the first embodiment of the present invention.

FIG. 1 is a block diagram showing a configuration of a medical imaging system according to the first embodiment of the present invention. The medical imaging system includes a combination of a radiation mammography apparatus for applying radiation to a breast and generating radiation images by detecting radiation transmitted through the breast, and an ultrasonic diagnostic apparatus for transmitting ultrasonic waves to the breast and generating ultrasonic images by receiving ultrasonic waves reflected within the breast. In the embodiment, X-rays are used as radiation.

The medical imaging system shown in FIG. 1 includes an X-ray imaging control section 100, an X-ray tube 110, a filter unit 111, an X-ray detection unit 120, an ultrasonic imaging control section 200, an ultrasonic probe 210, an imaging condition control section 300, a control unit 400, a console 410, a storage unit 420, a digital/analog converter (D/A) 431, and a display unit 432. Here, the X-ray tube 110, the filter unit 111, the X-ray detection unit 120, and the ultrasonic probe 210 configure an imaging section.

The X-ray imaging control section 100, the X-ray tube 110, the filter unit 111, and the X-ray detection unit 120 perform X-ray mammography (X-ray imaging), and the ultrasonic imaging control section 200 and the ultrasonic probe 210 perform ultrasonic imaging.

Figure 2:
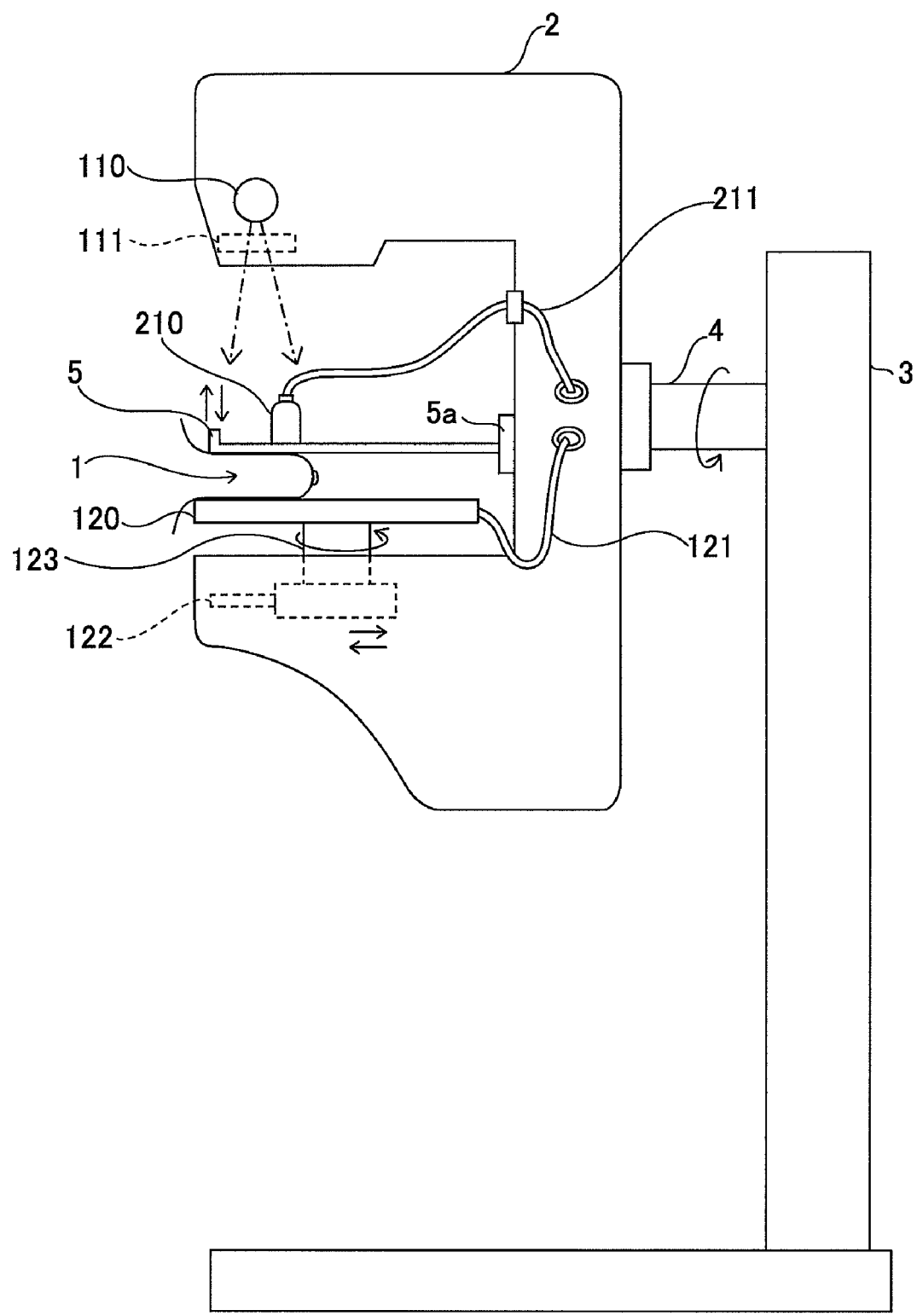
FIG. 2 is a side view showing an appearance of the imaging section of the medical imaging system shown in FIG. 1.

FIG. 2 is a side view showing an appearance of the imaging section of the medical imaging system shown in FIG. 1. The imaging section of the medical imaging system includes an arm part 2 in which the X-ray tube 110, the filter unit 111, the X-ray detection unit 120, and the ultrasonic probe 210 are provided, a base 3, and a shaft part 4 for rotatably holding the arm part 2 to the support base 3.

The X-ray detection unit 120 is a flat panel X-ray detector having plural X-ray detecting elements two-dimensionally arranged on a surface. When an X-ray radiated from the X-ray tube 110 and transmitted through the object is applied to each X-ray detecting element, the element outputs a detection signal having a magnitude corresponding to the intensity of the X-ray. These detection signals are outputted to the X-ray imaging control section 100 shown in FIG. 1 via a cable 121. Further, the X-ray detection unit 120 is provided with a position adjustment part 122 that moves the X-ray detection unit 120 in the horizontal direction, and a direction adjustment part 123 that turns the X-ray detection unit 120 within a horizontal plane.

A compression plate 5 is attached to the arm part 2 via a compression plate drive part 5a. The compression plate 5 is provided movably in the vertical direction in parallel to the X-ray detection unit 120. An object to be inspected (breast) 1 is sandwiched by the compression plate 5 and the X-ray detection unit 120 to make the thickness of the breast uniform, and then, X-ray imaging is performed thereon. The compression plate 5 is formed of a material that transmits the X-ray radiated from the X-ray tube 110 and easily propagates ultrasonic waves to be transmitted from and received by the ultrasonic probe 210. For example, resin materials such as acryl, polycarbonate, polyethylene terephthalate, and polymethylpentene are nearly transparent to X-rays and have acoustic impedances of about $1.5 \times 10^6$ Ns/m$^3$ to $5.0 \times 10^6$ Ns/m$^3$, and they can suppress the reflection of ultrasonic waves to relatively low levels.

The ultrasonic probe 210 includes one-dimensionally or two-dimensionally arranged plural ultrasonic transducers. These ultrasonic transducers transmit ultrasonic waves to the object based on applied drive signals, and receive ultrasonic echoes reflected from the object to output reception signals.

Each ultrasonic transducer is configured by a vibrator in which electrodes are formed on both ends of a material having a piezoelectric property (piezoelectric material) such as a piezoelectric ceramic represented by PZT (Pb (lead) zirconate titanate), a polymeric piezoelectric element represented by PVDF (polyvinylidene difluoride), or the like. When a voltage is applied to the electrodes of the vibrator by transmitting pulsed or continuous wave electric signals, the piezoelectric material expands and contracts. By the expansion and contraction, pulsed or continuous wave ultrasonic waves are generated from the respective vibrators, and an ultrasonic beam is formed by synthesizing these ultrasonic waves. Further, the respective vibrators expand and contract by receiving propagating ultrasonic waves and generate electric signals. These electric signals are outputted as reception signals of the ultrasonic waves, and outputted to the ultrasonic imaging control section 200 shown in FIG. 1 via a cable 211.

Alternatively, as the ultrasonic transducers, plural kinds of elements of different ultrasonic conversion types may be used. For example, the above-mentioned vibrators are used as elements for transmitting ultrasonic waves and photo-detection type ultrasonic transducers are used as elements for receiving ultrasonic waves. The photo-detection type ultrasonic transducer is for detecting ultrasonic waves by converting the ultrasonic waves into optical signals, and configured by a Fabry-Perot resonator or fiber Bragg grating, for example.

Such an ultrasonic probe 210 is used in contact with the compression plate 5, and performs transmission and reception of ultrasonic waves to and from the object (breast) 1 via the compression plate 5. At that time, an examiner (operator) may hold the ultrasonic probe 210 to manually scan on the compression plate 5, or a holder and a drive mechanism may be provided for supporting the ultrasonic probe 210 for automatically scanning on the compression plate 5.

Referring to FIG. 1 again, the X-ray imaging control section 100 includes a tube-voltage/target/filter control unit 11, a high voltage generating unit 12, an exposure dose control unit 13, a pixel pitch control unit 14, an analog/digital converter (A/D) 15, and a radiation image data generating unit 16.

The tube-voltage/target/filter control unit 11 sets the magnitude of the voltage (tube voltage) to be applied to the X-ray tube 110 and the combination of materials of a target to be used in the X-ray tube 110 and a filter to be used in the filter unit 111 (e.g., tungsten/rhodium, molybdenum/molybdenum, molybdenum/rhodium, rhodium/rhodium, or the like), and thereby, controls X-ray characteristics. Further, the high voltage generating unit 12 generates a voltage to be applied to the X-ray tube 110 under the control of the tube-voltage/target/filter control unit 11. The exposure dose control unit 13 controls the X-ray dose applied from the X-ray tube 110 to the object. The pixel pitch control unit 14 sets the pixel pitch in the X-ray detection unit 120. Thereby, detection signals are outputted at intervals set by the pixel pitch control unit 14 from the plural X-ray detecting elements contained in the X-ray detection unit 120.

The analog/digital converter (A/D) 15 digital-converts the detection signals outputted from the X-ray detection unit 120 to output detection data. The radiation image data generating unit 16 generates X-ray image data representing the brightness in an X-ray image based on the detection data outputted from the analog/digital converter 15, and outputs the data to the storage unit 420 for accumulation. Simultaneously, the X-ray image data may be outputted to the D/A converter 431 to display an X-ray image on the display unit 432.

On the other hand, the ultrasonic imaging control section 200 includes a scan control unit 21, a transmission circuit 22, a reception circuit 23, an analog/digital converter (A/D) 24, a signal processing unit 25, a B-mode image data generating unit 26, and a digital scan converter (DSC) 27.

The scan control unit 21 sequentially sets a transmission direction of an ultrasonic beam or a reception direction of ultrasonic echoes, and has a transmission control function of selecting a transmission delay pattern according to the set transmission direction and a reception control function of selecting a reception delay pattern according to the set reception direction. Further, the scan control unit 21 includes a frequency control part 21a for setting the frequency of the ultrasonic waves to be transmitted from the ultrasonic probe 210, a drive voltage control part 21b for adjusting the power of the ultrasonic waves to be transmitted via drive voltages applied to the respective ultrasonic transducers of the ultrasonic probe 210, and a scan speed control part 21c for controlling electronic scan speed by the plural ultrasonic transducers.

Here, the transmission delay pattern refers to a pattern of delay times to be provided to the drive signals for forming an ultrasonic beam in a desired direction by the ultrasonic waves transmitted from the plural ultrasonic transducers of the ultrasonic probe 210, and the reception delay pattern refers to a pattern of delay times to be provided to the reception signals for extracting ultrasonic echoes from a desired direction by the ultrasonic waves received by the plural ultrasonic transducers. Plural transmission delay patterns and reception delay patterns are stored in a memory or the like.

The transmission circuit 22 generates drive signals to be respectively applied to the plural ultrasonic transducers. At that time, the transmission circuit 22 can provide respective delay times to the drive signals based on the transmission delay pattern selected by the scan control unit 21. Here, the transmission circuit 22 may adjust the amounts of delay of the drive signals and supply the drive signals to the ultrasonic probe 210 such that the ultrasonic waves to be transmitted from the plural ultrasonic transducers form an ultrasonic beam, or may supply drive signals to the ultrasonic probe 210 such that the ultrasonic waves to be transmitted at once from the plural ultrasonic transducers reach the entire imaging region of the object.

The reception circuit 23 amplifies the reception signals respectively outputted from the plural ultrasonic transducers, and the A/D converter 24 converts the analog reception signals amplified by the reception circuit 23 into digital reception signals. The digital reception signals outputted from the A/D converter 24 are inputted to the signal processing unit 25. The signal processing unit 25 performs reception focus processing by providing the respective delay times to the reception signals based on the reception delay pattern selected by the scan control unit 21, and adding those reception signals to one another. Through the reception focus processing, sound ray data, in which the focal point of the ultrasonic echoes is narrowed, is formed.

Furthermore, the signal processing unit 25 corrects attenuation of the sound ray data by distance according to the depths of the reflection positions of ultrasonic waves through STC (sensitivity time gain control), and then, performs envelope detection processing with a low-pass filter or the like thereon to generate envelope data.

The envelope data generated by the signal processing unit 25 is supplied to the B-mode image data generating unit 26 and temporarily stored. The B-mode image data generating unit 26 may have a memory capacity for storing envelope data for plural frames. The B-mode image data generating unit 26 performs pre-process processing such as Log(logarithmic) compression and gain adjustment on the stored envelope data to generate B-mode image data, and outputs the generated B-mode image data to the DSC 27.

The DSC 27 converts (raster-converts) the B-mode image data generated by the B-mode image data generating unit 26 into ultrasonic image data that follows the normal scan system of television signals to generate ultrasonic image data for display. Further, the DSC 27 outputs the ultrasonic image data to the D/A converter 431 for real time display of moving images or still images of the ultrasonic images and outputs the ultrasonic image data to the storage unit 420 for storage.

The imaging condition control section 300 includes an image processing unit 31, an X-ray imaging condition setting unit 32, and an ultrasonic imaging condition setting unit 33.

The image processing unit 31 includes a breast type determining part 31a and a CAD (computer aided detection) processing part 31b. The breast type determining part 31a analyzes an X-ray image represented by the X-ray image data outputted from the radiation image data generating unit 16 and an ultrasonic image represented by the ultrasonic image data outputted from the DSC 27, and thereby, determines whether the type of the breast on the images is dense breast or fat breast. On the other hand, the CAD processing part 31b analyzes the X-ray image and the ultrasonic image, and thereby, detects a lesion part (calcification or tumor mass) caused in the breast.

Further, the image processing unit 31 may perform image processing such as linear gradation processing including gain adjustment and contrast adjustment and nonlinear gradation processing including γ-correction on the X-ray image data and the ultrasonic image data. Furthermore, the image processing unit 31 outputs the X-ray image data and the ultrasonic image data to the D/A converter 431 so that the display unit 432 displays the X-ray image and the ultrasonic image. In this regard, the image processing unit 31 may output a detection result by the breast type determining part 31a and the CAD processing part 31b 431 so that the display unit 432 displays them with the X-ray image and/or the ultrasonic image.

The X-ray imaging condition setting unit 32 sets imaging condition (tube voltage, combination of target and filter, exposure dose, pixel pitch, application direction of X-ray, or the like) in X-ray imaging to be performed after ultrasonic imaging, based on the analysis result made on the ultrasonic image by the breast type determining part 31a and/or the CAD processing part 31b. Further, the ultrasonic imaging condition setting unit 33 sets imaging condition (frequency and power of transmission ultrasonic waves, scan speed, or the like) in ultrasonic imaging to be performed after X-ray imaging based on the analysis result made on the X-ray image by the breast type determining part 31a or the CAD processing part 31b.

The control unit 400 controls the entire medical imaging system according to the embodiment. Further, the console 410 is an input device to be used by the examiner (operator) when inputting various kinds of commands and information to the medical imaging system. Furthermore, the storage unit 420 is configured by a hard disk, memory, or the like, and stores an operational program for activating a CPU contained in the medical imaging system to execute operations and programs (software) to be used for various kinds of processing, information to be used for the processing, and so on.

The D/A converter 431 converts the X-ray image data and the ultrasonic image data outputted from the image processing unit 31 and/or the ultrasonic image data for display outputted from the DSC 27 into analog signals and outputs them to the display unit 432.

The display unit 432 is a raster-scan type CRT display or LCD display, and displays X-ray images and/or moving images or still images of ultrasonic images based on the image signals analog-converted in the D/A converter 431. Although one D/A converter and one display unit are provided in the embodiment, two or more converters and two or more display units may be provided for displaying the X-ray image and the ultrasonic image separately.

In the embodiment, the radiation image data generating unit 16, the scan control unit 21, the signal processing unit 25, the B-mode image data generating unit 26, the DSC 27, the image processing unit 31, the X-ray imaging condition setting unit 32, the ultrasonic imaging condition setting unit 33, and the control unit 400 are configured by a central processing unit (CPU) and software for activating the CPU to execute various kinds of processing. However, they may be configured by a digital circuits or analog circuits. The above software is stored in the storage unit 420. In addition, the transmission delay patterns and the reception delay patterns to be selected by the scan control unit 21 may be stored in the storage unit 420.

Figure 3:
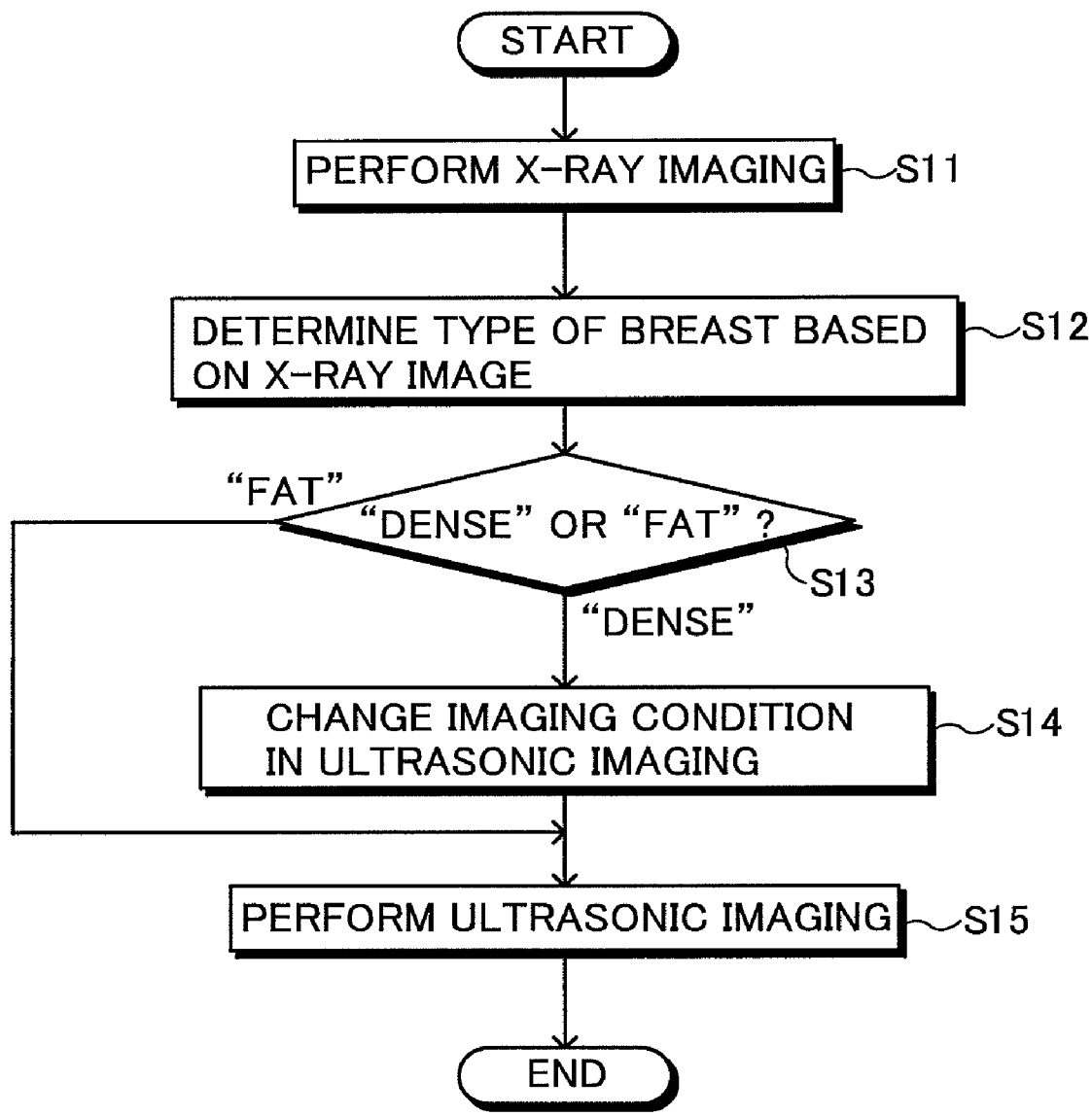
FIG. 3 is a flowchart showing a medical imaging method according to the first embodiment of the present invention.
Figure 4A:
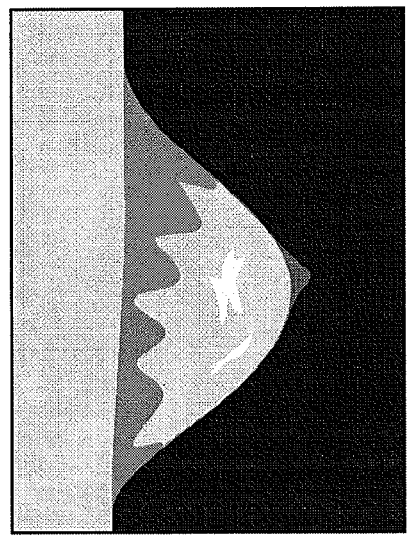
FIGS. 4A and 4B are schematic diagrams showing X-ray mammograms.
Figure 4B:
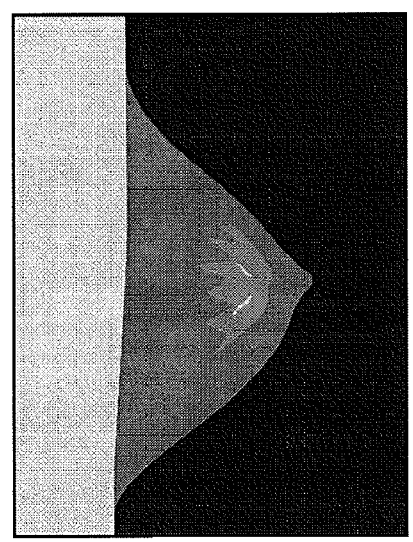

Next, a medical imaging method according to the first embodiment of the present invention will be explained with reference to FIGS. 1, 3, 4A and 4B. FIG. 3 is a flowchart showing the medical imaging method according to the first embodiment of the present invention. Further, FIGS. 4A and 4B are schematic diagrams showing X-ray images (X-ray mammograms) obtained by X-ray mammography.

First, at step S11, X-ray imaging (X-ray mammography) of a breast is performed by using the X-ray imaging control section 100, the X-ray tube 110, the filter unit 111, and the X-ray detection unit 120 shown in FIG. 1. As the imaging condition (tube voltage, combination of target and filter, exposure dose, pixel pitch, or the like), standard preset values may be used or an operator may arbitrarily set them from experience. X-ray image data obtained by X-ray imaging is temporarily stored in the storage unit 420 shown in FIG. 1.

Then, at step S12, the image processing unit 31 reads out the X-ray image data from the storage unit 420. Subsequently, the breast type determining part 31a determines the type of the breast ("dense" or "fat") shown in the X-ray image represented by the X-ray image data.

The determination of breast type is performed in the following manner. First, the breast type determining part 31a extracts a region, where the breast is shown, from the X-ray image represented by the X-ray image data. For example, a pixel having a value of X-ray image data that is equal to or larger than a predetermined value and has a difference between values of X-ray image data in surrounding pixels and itself equal to or larger than a predetermined value is determined to be a boundary of the breast region.

Then, the breast type determining part 31a determines the type of the extracted breast based on the brightness (or lightness from white to black) of the pixel within the breast region. Here, in the breast of a premenopausal woman, mammary glands that easily absorb X-rays have developed. Accordingly, as shown in FIG. 4A, her breast is shown whitish as a whole in the X-ray image. On the other hand, mammary gland tissues have become atrophied in the breast of a postmenopausal woman, few X-rays are absorbed. Accordingly, as shown in FIG. 4B, her breast is shown blackish as a whole. Therefore, the breast type determining part 31a obtains a histogram on the data values in the respective pixels within the breast region, and further, obtains a value as a barycenter. If the barycenter value is equal to or larger than a predetermined threshold value, the breast is determined to be "dense", and, if the barycenter value is less than the predetermined threshold value, the breast is determined to be "fat".

If the breast is determined to be "dense" at step S13 in FIG. 3, then at step S14, the ultrasonic imaging condition setting unit 33 changes the imaging condition in ultrasonic imaging such that the "dense" breast is easily diagnosed. This is because the diagnosis of the "dense" breast is generally difficult. Accordingly, for example, the scan speed is reduced for detailed observation, or the output power of ultrasonic waves is raised by increasing the drive voltages of the ultrasonic transducers for improvement of S/N-ratio. Then, at step S15, ultrasonic imaging is performed by the ultrasonic imaging control section 200 and the ultrasonic probe 210 under imaging condition that has been newly set.

On the other hand, if the breast is determined to be "fat" at step S13, ultrasonic imaging is performed without any changes in the imaging condition (step S15).

As described above, according to the embodiment, the imaging condition in ultrasonic imaging is changed according to the breast type determined based on the X-ray image. Therefore, appropriate medical diagnoses can be made based on X-ray images and ultrasonic images obtained under appropriate condition, and detection accuracy and examination efficiency for breast cancer can be improved.

Figure 5:
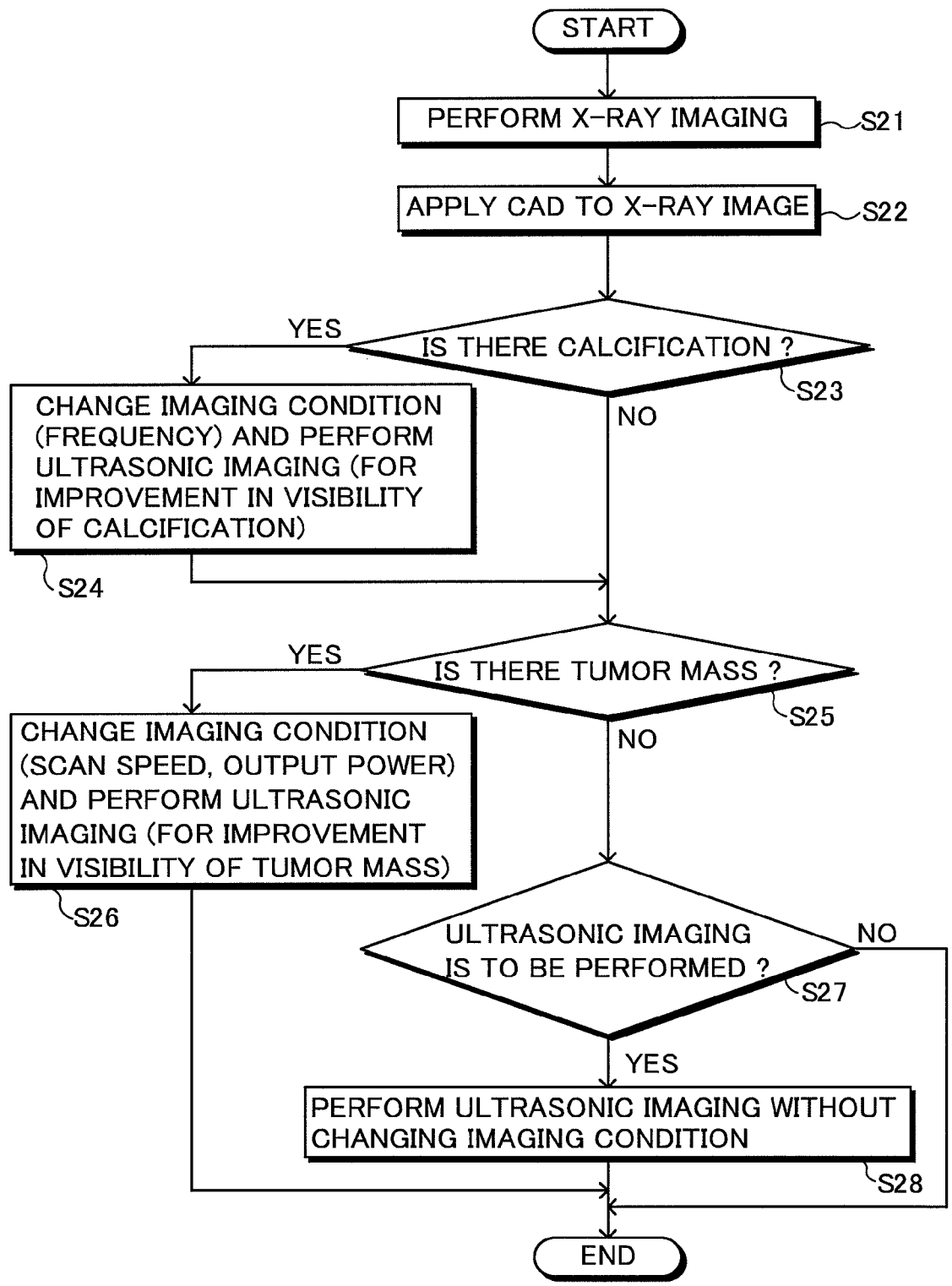
FIG. 5 is a flowchart showing a medical imaging method according to the second embodiment of the present invention.

Next, a medical imaging method according to the second embodiment of the present invention will be explained with reference to FIGS. 1, and 5-8. FIG. 5 is a flowchart showing the medical imaging method according to the second embodiment of the present invention.

First, at step S21, X-ray imaging is performed on a breast by using the X-ray imaging control section 100, the X-ray tube 110, the filter unit 111, and the X-ray detection unit 120 shown in FIG. 1, and thus obtained X-ray image data is temporarily stored in the storage unit 420. As imaging condition (tube voltage, combination of target and filter, exposure dose, pixel pitch, or the like), standard preset values may be used or an operator may arbitrarily set them.

Then, at step S22, the image processing unit 31 reads out the X-ray image data from the storage unit 420. Subsequently, the CAD processing part 31b detects from an X-ray image a lesion part such as calcified region or tumor mass or a part suspected to be a lesion.

(i) Detection of Calcified Region

In a general breast X-ray image, the calcified part has higher brightness (lower density) than in the background and takes on a sharply pulsed shadow with jagged outlines. Accordingly, by performing differential processing on the X-ray image, a region having high differential value and brightness can be detected as a calcified region.

Further, for calcified region detection with higher accuracy, for example, morphology processing applying mathematical morphology may be used.

Here, the mathematical morphology will be explained.

First, the assumption is that a gray-scale image (X-ray image) is a space in which a point of coordinates (x, y) has a height corresponding to a density value f (x, y). Here, the lower the density (i.e., the higher the brightness), the larger the density value f(x, y) becomes.

For ease of explanation, one-dimensional function f (x) with respect to density value (i.e., the section of gray-scale image) is considered. The structural element "g" used in mathematical morphology is a symmetry function symmetric with respect to origin as expressed in the following equation.

$$g^s(x) = g(-x) \quad (1)$$

Further, its domain G is as follows.

$$G = \{-m, -m+1, \ldots, -1, 0, 1, \ldots, m-1, m\}$$

In this regard, the basic operations of mathematical morphology are shown in FIG. 6. As shown in FIG. 6, dilation processing is processing of retrieving the maximum value in the width of m (the value determined according to the structural element) around a pixel of interest as a center position, and erosion processing is processing of retrieving the minimum value in the width of m around a pixel of interest as a center position. Further, opening processing is processing of retrieving the maximum value after retrieving the minimum value. That is, the processing smoothes the density curve f(x) from the low brightness side and removes the convex density variation part (the region having higher brightness than surroundings) that varies in a range spatially narrower than a predetermined mask size. Furthermore, closing processing is processing of retrieving the minimum value after retrieving the maximum value. That is, the processing smoothes the density curve f(x) from the high brightness side and removes the concave density variation part (the region having lower brightness than surroundings) that varies in a range spatially narrower than a predetermined mask size.

By performing such mathematical morphology on an X-ray image, a smoothed image is obtained. Then, by subtracting the smoothed image from the original image, an image in which the shadow of the calcified region has been extracted can be obtained.

(ii) Extraction of Tumor Mass

Generally, in an X-ray image, the shadow of a tumor mass is slightly lower in density (i.e., higher in brightness) than the surroundings, and the gradient vector in an arbitrary pixel is directed toward the center of the tumor mass shadow. Accordingly, the CAD processing part 31b calculates the density gradient in the X-ray image and obtains the degree of concentration of gradient vectors, and thereby, extracts a candidate region of abnormal shadow. The degree of concentration of gradient vectors is evaluated by using an iris filter, for example.

Figures 7, 8:
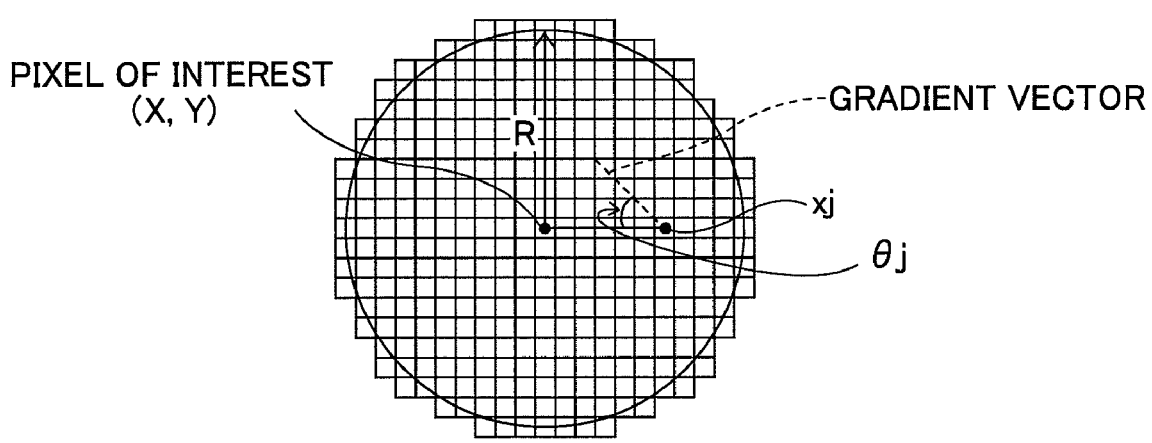
FIG. 7 is a diagram for explanation of tumor mass detection processing using evaluation on degree of concentration of gradient vectors by an iris filter.
FIG. 8 is a diagram for explanation of tumor mass detection processing using evaluation on degree of concentration of gradient vectors by the iris filter.

The tumor mass detection processing using the evaluation of the degree of concentration of gradient vectors with an iris filter will be explained with reference to FIGS. 7 and 8. First, with respect to each pixel, amounts of density change in x-direction and y-direction are obtained, and thereby, direction $\theta_j$ of the gradient vector in a certain pixel $x_j$ is calculated. For the calculation, for example, a mask having a size of 5×5 pixels (gradient vector calculation mask) shown in FIG. 7 and the following equation (2) are used. In FIG. 7 and the equation (2), $f_1, f_2, \ldots$ represent data values (pixel values) in pixels surrounding the certain pixel $x_j$.

$$\theta_j = \tan^{-1} \frac{(f_3 + f_4 + f_5 + f_6 + f_7) - (f_{11} + f_{12} + f_{13} + f_{14} + f_{15})}{(f_1 + f_2 + f_3 + f_{15} + f_{16}) - (f_7 + f_8 + f_9 + f_{10} + f_{11})} \quad (2)$$

Then, with respect to each pixel forming the image as a detection subject of tumor mass, the degree of concentration "C" of gradient vectors is obtained by the following equation (3).

$$C = \frac{1}{N} \sum_{j=1}^{N} \cos \theta_j \quad (3)$$

Here, referring to FIG. 8, in the equation (3), N is the number of pixels present within a circle around a pixel of interest (X, Y) with radius R, and $\theta_j$ is an angle formed by a straight line connecting the pixel of interest (X, Y) and the certain pixel $x_j$ and the gradient vector at the pixel $x_j$, which has been calculated by the equation (2).

The degree of concentration "C" of gradient vectors obtained by the equation (3) becomes large when the gradient vectors in the respective pixels are concentrated on the pixel of interest. Further, the gradient vector $\theta_j$ in the pixel near the tumor mass shadow is generally directed toward the center of the tumor mass regardless of the contrast of the tumor mass shadow. Therefore, the pixel of interest having a large value of degree of concentration "C" of gradient vectors can be determined to be a central part of the tumor mass shadow.

Contrary, in the linear pattern shadow of a blood vessel or the like, the directions of the gradient vectors are biased toward one direction, and the degree of concentration "C" of gradient vectors becomes small. Therefore, by setting a threshold value of the degree of concentration "C" of gradient vectors and comparing the degree of concentration "C" of gradient vectors obtained with respect to each pixel forming an X-ray image with a threshold value, a pixel region in which the degree of concentration "C" of gradient vectors is larger than the threshold value can be detected as a tumor mass shadow.

(iii) Method Using Template Matching

As described above, the calcified region has a sharply pulsed shape with jagged outlines. On the other hand, the tumor mass in the breast has a round shape with smooth outlines. Therefore, the calcified region and tumor mass can be detected by preparing templates having those shapes and utilizing correlation values obtained by matching with the outlines extracted in the X-ray image as evaluation values. For outline extraction, known methods such as methods using pixel values and their differential values may be used.

As a method of extracting a calcified region and a tumor mass region, various known image processing methods other than the morphology processing, the iris filter processing, and the template matching may be applied.

Referring to FIG. 5 again, if a calcified region or a region suspected to be calcified is detected at step S23, then at step S24, the ultrasonic imaging condition setting unit 33 changes the imaging condition in ultrasonic imaging. Thereby, ultrasonic imaging is performed by the ultrasonic imaging control section 200 and the ultrasonic probe 210 under the condition. Specifically, the ultrasonic imaging condition setting unit 33 controls the frequency control part 21a to heighten the frequency of transmission ultrasonic waves. Thereby, the axial resolving power is increased, so that the minute structures of the object can be observed. Alternatively, the ultrasonic imaging condition setting unit 33 may control the frequency control part 21a to heighten the frequency in the region where the calcification has been recognized and lower the frequency in other regions. Thereby, the minute structures can be observed in the lesion and the wide region over the depth part can be observed in the other regions.

Then, if a tumor mass or a part suspected to be a tumor mass is detected at step S25, the ultrasonic imaging condition setting unit 33 changes the imaging condition in ultrasonic imaging at step S26. Thereby, ultrasonic imaging is performed under the changed condition. Specifically, the ultrasonic imaging condition setting unit 33 controls the scan speed control part 21c to lower the scan speed so that detailed observation can be performed on the object. Alternatively, the ultrasonic imaging condition setting unit 33 may control the drive voltage control part 21b to increase the output power of ultrasonic waves by raising the drive voltages of the ultrasonic transducers. In this case, the S/N-ratio in the ultrasonic image is improved.

If neither a calcified region (step S23) nor a tumor mass (step S25) is detected from the X-ray image, the operator determines whether or not the ultrasonic imaging is to be subsequently performed (step S27). If ultrasonic imaging is performed, there is no need to change the imaging condition (step S28). However, the operator may arbitrarily set the imaging condition from experience. Alternatively, if the operator determines that ultrasonic imaging is not necessary, ultrasonic imaging may not be performed at step S28.

As described above, according to the embodiment, if a lesion or a part suspected to be a lesion is detected from an X-ray image, the imaging condition in ultrasonic imaging are changed according to the status of the detected part, and thus, efficient examinations can be performed. Further, appropriate medical diagnoses can be made based on X-ray images and ultrasonic images obtained in this manner.

Figure 9:
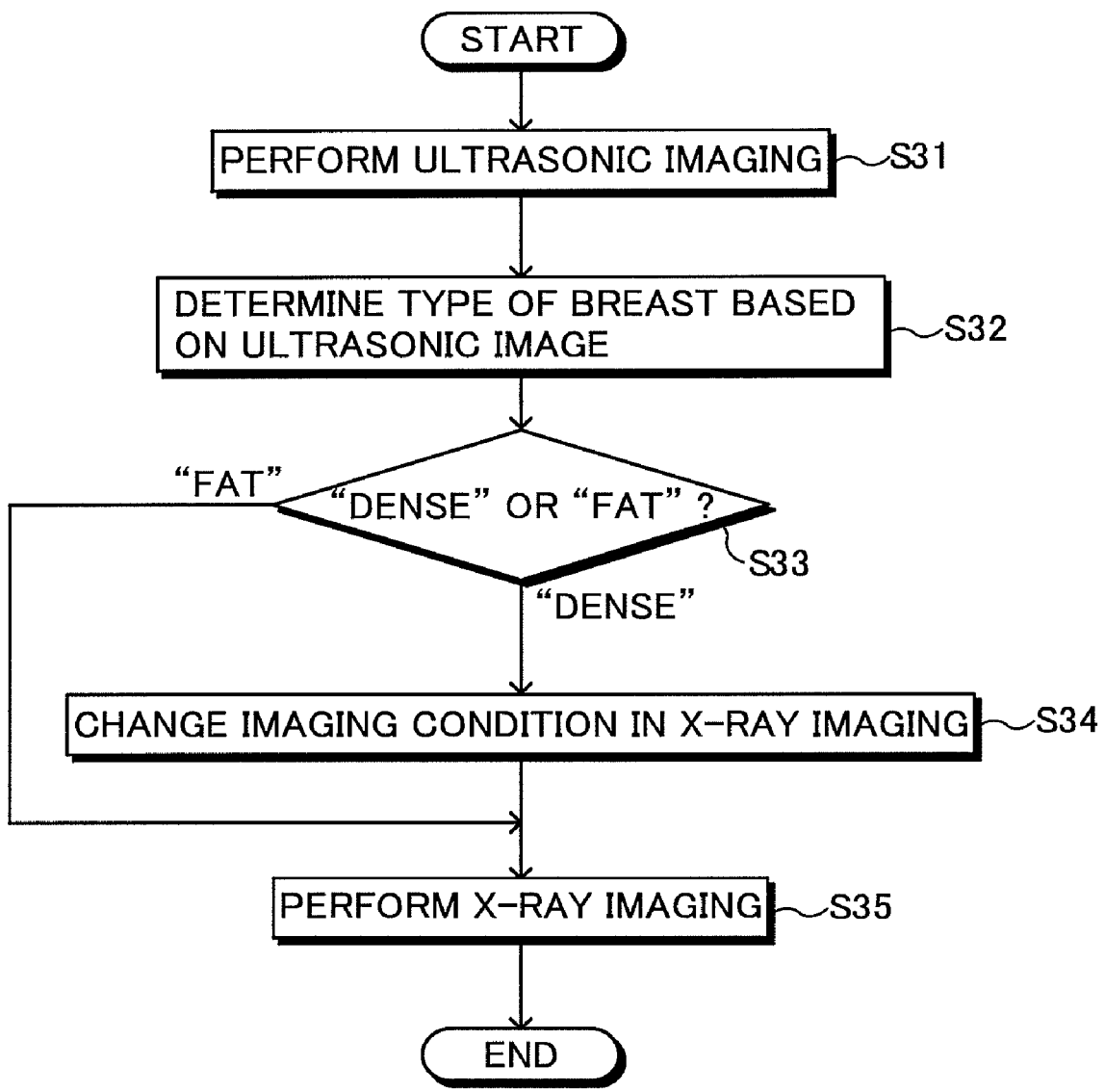
FIG. 9 is a flowchart showing a medical imaging method according to the third embodiment of the present invention.
Figure 10A:
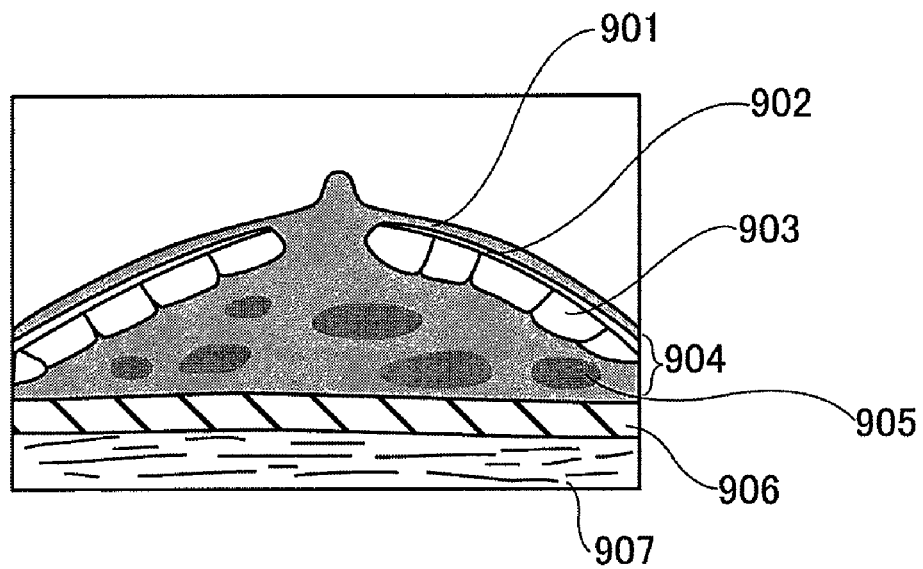
FIGS. 10A and 10B are schematic diagrams showing ultrasonic images representing breast sections.
Figure 10B:
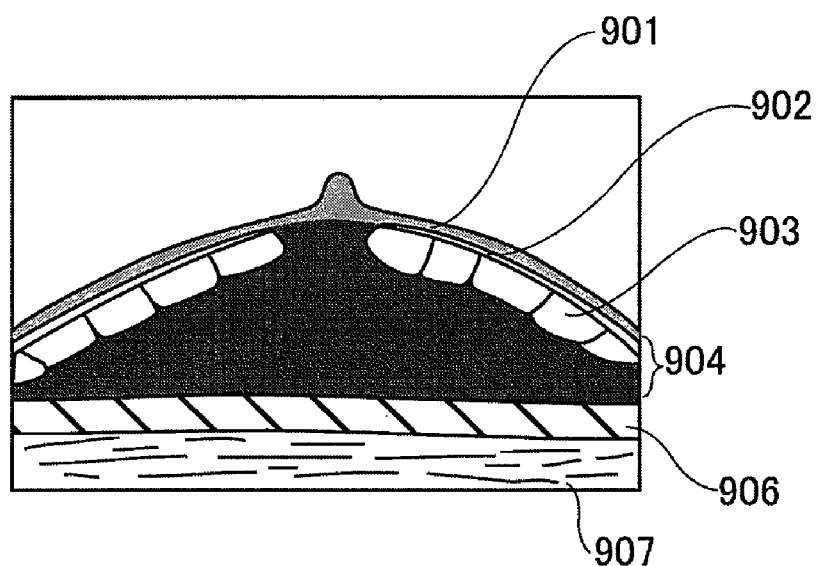

Next, a medical imaging method according to the third embodiment of the present invention will be explained with reference to FIGS. 1, 9, 10A and 10B. FIG. 9 is a flowchart showing the medical imaging method according to the third embodiment of the present invention. Further, FIGS. 10A and 10B are schematic diagrams showing ultrasonic images representing breast sections.

First, at step S31, ultrasonic imaging of a breast is performed by using the ultrasonic imaging control section 200 and the ultrasonic probe 210 shown in FIG. 1. As imaging condition (frequency of transmission ultrasonic waves, drive voltage, scan speed, or the like), standard preset values may be used or an operator may arbitrarily set them from experience. Ultrasonic image data obtained by ultrasonic imaging is temporarily stored in the storage unit 420 shown in FIG. 1. Further, the ultrasonic image data is also outputted to the DSC 27, and thereby, ultrasonic images are displayed in real time on the display unit 432.

Then, at step 32, the image processing unit 31 reads out the ultrasonic image data from the storage unit 420. Subsequently, the breast type determining part 31a determines the type of the breast ("dense" or "fat") shown in the ultrasonic image represented by the ultrasonic image data.

A method of determining the breast type will be explained with reference to FIGS. 10A and 10B. As shown in FIGS. 10A and 10B, the breast has a structure including from the surface layer a skin 901, a superficial fascia shallow layer 902, a Cooper's ligament 903, a subcutaneous fat layer 904, a mammary gland layer 905, a superficial fascia deep layer 906, and a pectoral major muscle superficial fascia 907. As shown in FIG. 10A, since the mammary glands 905 have developed in a premenopausal object, the mammary gland layer 905 is observed as mottled tissues in the ultrasonic image. On the other hand, as shown in FIG. 10B, since the mammary glands have become atrophied in a postmenopausal object, uniform fat tissues (subcutaneous fat layer 904) are observed in the ultrasonic image. In the embodiment, the breast type is determined based on the feature of the mammary glands.

First, in the ultrasonic image, the pectoral major muscle superficial fascia having a layer structure is extracted by searching from the breast surface layer. Specifically, the area having repeated edges is retrieved. Alternatively, template matching may be performed by using a layer-formed template. Thereby extracted region above the pectoral major muscle superficial fascia (toward the skin side) is assumed to be a mammary gland tissue.

Then, template matching is performed on the region that has been assumed to be a mammary gland tissue by using a circular or oval template. Here, as described above, in the mammary glands, mottled tissues, i.e., nearly circular or oval tissues are observed. Therefore, if the determination subject is "dense", the evaluation value by the template matching is high. Accordingly, the breast type determining part 31a obtains an evaluation value by template matching. If the evaluation value is equal to or larger than a predetermined threshold value, the breast type determining part 31a determines that the breast is "dense". If the evaluation value is less than the predetermined threshold value, the breast type determining part 31a determines that the breast is "fat".

If the breast is determined to be "dense" at step S33, then at step S34, the X-ray imaging condition setting unit 32 changes the imaging condition in X-ray imaging such that the "dense" breast is easily diagnosed. Specifically, for example, the tube voltage may be lowered to increase the contrast, or the target may be set to molybdenum. Then, at step S35, X-ray imaging is performed by the X-ray imaging control section 100, the X-ray tube 110, and the X-ray detection unit 120 under imaging condition that has been newly set.

On the other hand, if the breast is determined to be "fat" at step S33, X-ray imaging is performed without any changes in the imaging condition. Alternatively, for the "fat" breast, the imaging condition in X-ray imaging may be changed such that the tube voltage is raised for suppressing the exposure or the target may be tungsten.

As described above, according to the embodiment, the imaging condition in X-ray imaging is changed according to the breast type determined based on the ultrasonic image. Therefore, appropriate medical diagnoses can be made based on ultrasonic images and X-ray images obtained under appropriate condition, and detection accuracy and examination efficiency for beast cancer can be improved.

Figure 11:
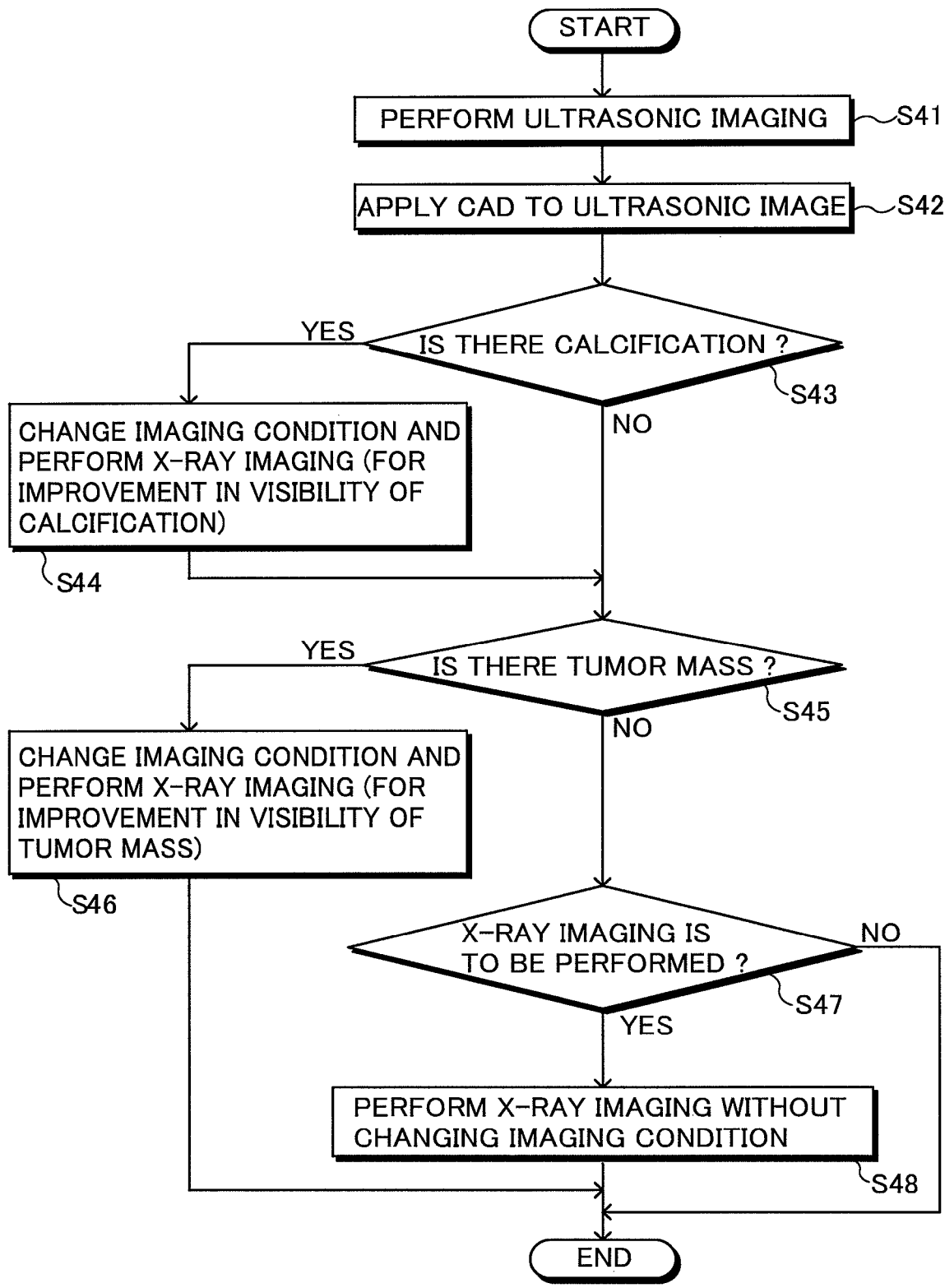
FIG. 11 is a flowchart showing a medical imaging method according to the fourth embodiment of the present invention.

Next, a medical imaging method according to the fourth embodiment of the present invention will be explained with reference to FIG. 11. FIG. 11 is a flowchart showing the medical imaging method according to the fourth embodiment of the present invention.

First, at step S41, ultrasonic imaging is performed on a breast by using the ultrasonic imaging control section 200 and the ultrasonic probe 210 shown in FIG. 1, and thus obtained ultrasonic image data is temporarily stored in the storage unit 420. As imaging condition (frequency, drive voltage, scan speed, or the like), standard preset values may be used or an operator may arbitrarily set them.

Then, at step S42, the image processing unit 31 reads out the ultrasonic image data from the storage unit 420. Subsequently, the CAD processing part 31b detects a lesion part or a part suspected to be a lesion from an ultrasonic image by using dynamic outline extraction. Alternatively, the operator may find the lesion by visually observation of the ultrasonic image displayed on the display unit 432.

Then, if a calcified region or a region suspected to be calcified is detected at step S43, then at step S44, the X-ray imaging condition setting unit 32 changes the imaging condition in X-ray imaging such that the visibility of the calcified region is improved (e.g., the tube voltage is lowered to increase contrast, the target/filter is set to the combination of molybdenum/molybdenum, the exposure dose is raised for imaging with high S/N-ratio, or the like). Thereby, X-ray imaging is performed by using the X-ray imaging control section 100, the X-ray tube 110, and the X-ray detection unit 120 under the imaging condition. Alternatively, though image capacity is reduced by coarse pixels (e.g., one pixel=about 100 μm) in a normal x-ray imaging, the X-ray imaging condition setting unit 32 controls the pixel pitch control unit 14 to reduce the pixel pitch (e.g., one pixel=about 50 μm). Thereby, a detailed X-ray image can be obtained for the object suspected to have a lesion.

Then, at step S45, if a tumor mass or a part suspected to be a tumor mass is detected from the ultrasonic image at step S45, then at step S46, the X-ray imaging condition setting unit 32 changes the imaging condition in X-ray imaging such that the visibility of the tumor mass is improved (e.g., the tube voltage is lowered to increase contrast, the target/filter is set to the combination of molybdenum/molybdenum, the exposure dose is raised for imaging with high S/N-ratio, or the like). Thereby, X-ray imaging is performed under the imaging condition.

If neither a calcified region (step S43) nor a tumor mass (step S45) is detected from the ultrasonic image, the operator determines whether or not the X-ray imaging is to be subsequently performed (step S47). If X-ray imaging is performed, there is no need to change the imaging condition (step S48). However, the operator may arbitrarily set the imaging condition from experience. Further, if the operator determines that X-ray imaging is not necessary, ultrasonic imaging may not be performed at step S48.

Next, a first modified example of the medical imaging method according to the fourth embodiment of the present invention will be explained.

In the fourth embodiment, if a tumor mass is detected at step S45 in FIG. 11, the imaging condition is changed and X-ray imaging is performed (step S46), while, in the first modified example, imaging for generating an energy subtraction image is performed in place of typical X-ray imaging.

Here, the energy subtraction image is an image generated by generating two kinds of X-ray images based on X-rays generated under different condition and subtracting pixel values of the second X-ray image from pixel values of the first X-ray image. In typical X-ray imaging, normal mammary gland tissues, other soft tissues, tumors, and so on overlap, and it may be difficult to separate and observe the lesion part. However, those respective tissues are different from one another in X-ray absorption characteristics, and thus, particular tissues (structures) can be extracted and observed by subtraction of X-ray images obtained based on X-rays having different characteristics.

In the first modified example, the X-ray imaging condition setting unit 32 sets two kinds of different imaging condition, and X-ray imaging is performed twice under the respective kinds of different imaging condition. Specifically, X-ray imaging is performed by using a high-energy transmission filter (e.g., a strontium filter, strontium compound filter, or the like) for the first time, and X-ray imaging is performed by using a low-energy transmission filter (e.g., a molybdenum filter, molybdenum compound filter, or the like) for the second time. Thereby, an X-ray image taken with the high energy component of X-ray and an X-ray image taken with the low energy component of X-ray can be obtained.

Alternatively, between the first imaging and the second imaging, the energy component of X-ray may be changed by changing the magnitude of the tube voltage. Thus obtained two kinds of X-image data are temporarily stored in the storage unit 420 and subtraction operation is performed thereon in the image processing unit 31. Thereby, image data representing a subtraction image is generated.

Further, in the first modified example, the X-ray imaging condition setting unit 32 may set the imaging condition for the two X-ray imagings, that is, tube voltage, target/filter, or the like based on the analysis result (size and shape of tumor mass) on the ultrasonic image that has been acquired.

Next, a second modified example of the medical imaging method according to the fourth embodiment of the present invention will be explained. In the second modified example, tomosynthesis imaging is performed in place of the typical X-ray imaging at step S46 in FIG. 11. The tomosynthesis imaging is a method of generating a tomographic image representing a desired section of the object by applying X-rays to the object 1 from different angles while moving the X-ray tube 110 (FIG. 1) to perform X-ray imaging at plural times and adding thus obtained X-ray images to one another. The addition processing of X-ray images is performed in the image processing unit 31.

Figure 12:
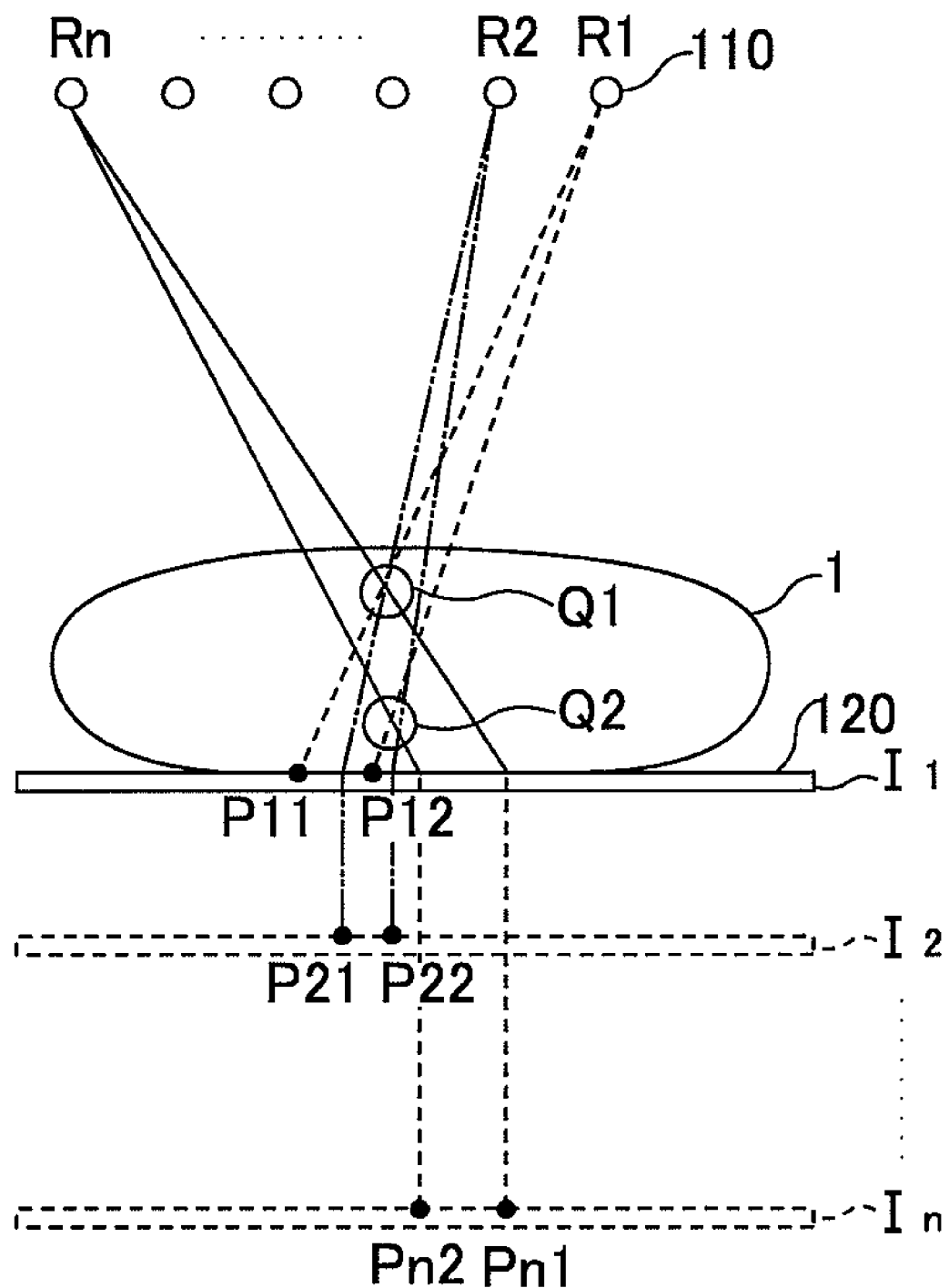
FIG. 12 is a diagram for explanation of an imaging principle of tomosynthesis imaging.

As shown in FIG. 12, for example, with an X-ray radiated from a position R1, an image I1 is generated in which information on a point Q1 and information on a point Q2 at different depths within the object are represented at points P11 and P12 on the X-ray detection unit 120. Further, with an X-ray radiated from a position R2, an image 12 is generated in which information on a point Q1 and information on a point Q2 at different depths within the object are represented at points P21 and P22 on the X-ray detection unit 120. Furthermore, with an X-ray radiated from a position R3, an image 13 is generated in which information on a point Q1 and information on a point Q2 at different depths within the object are represented at points Pn1 and Pn2 on the X-ray detection unit 120.

In order to highlight the section where the point Q1 is present within the object, add "an image formed by shifting the image 12 by (P21−P11)", . . . , "an image formed by shifting the image In by (Pn1−P11)" to one another. Thereby, a tomographic image including the point Q1 within the object is generated. Similarly, in order to highlight the section where the point Q2 is present within the object, add "an image formed by shifting the image 12 by (P22-P12)", . . . , "an image formed by shifting the image In by (Pn2-P12)" to one another. Thereby, a tomographic image including the point Q2 within the object is generated.

In the second modified example, the X-ray imaging condition setting unit 32 may set the imaging condition for the tomosynthesis imaging, that is, time intervals of imaging, angle of the arm part 2 (FIG. 2), i.e., application angle of X-ray, or the like based on the analysis result (tumor mass size or the like) on the ultrasonic image that has been previously acquired. Furthermore, the image processing unit 31 may determine the section shown in the tomographic image based on the analysis result (tumor mass position or the like) on the ultrasonic image that has been previously acquired.

Next, a first modified example of the medical imaging system (FIG. 1) according to the first embodiment of the present invention will be explained with reference to FIG. 13.

In the medical imaging system shown in FIG. 1, an X-ray transmitted through the object 1 is detected by using the X-ray detection unit 120. On the other hand, in the first modified example, as shown in FIG. 13, X-ray imaging is performed by using a recording sheet 130 coated with photostimulable phosphor and an image reading apparatus 140.

Here, the recording sheet 130 is a sheet coated with a photostimulable phosphor material. The photostimulable phosphor material has a nature that it accumulates part of energy of applied radiation (X-ray), and afterwards, when excitation light such as a laser beam is applied thereto, emits light (photostimulated luminescence) according to the accumulated energy. On the other hand, the image reading apparatus 140 is an apparatus of photoelectrically reading X-ray image information by scanning the recording surface of the recording sheet 130 with a laser beam and detecting thus photostimulated luminescence light with a photomultiplier to convert the light into an electric signal.

Accordingly, the image reading apparatus 140 is connected to the X-ray imaging control section 100 and the recording sheet 130 is provided in place of the X-ray detection unit 120 (FIG. 2), and then, X-ray imaging is performed. Subsequently, the imaged recording sheet 130 is inserted into the image reading apparatus 140 and the information recorded there is read, and then, the detection signal outputted from the image reading apparatus 140 is processed in the X-ray imaging control section 100 and the image processing unit 31.

Next, a second modified example of the medical imaging system (FIG. 1) according to the first embodiment of the present invention will be explained. Although the recording sheet coated with a photostimulable phosphor material is used in the first modified example, an electrostatic recording sheet that records X-ray image information as an electrostatic latent image is used instead thereof in the second modified example.

The electrostatic recording sheet is formed by stacking in the following order a first conductor layer having transmission to X-rays, an X-ray conducting layer (e.g., a material containing a-Se, PbO, $PbI_2$, $Bi_{12}(Ge,Si)O_{20}$, $Bi_2I_3$/organic polymer nano-composite, or the like) that exhibits photoconductivity on reception of X-ray application, a charge transport layer (e.g., a material containing PVK, TPD, polymer disperse material of TPD, Cl-doped a-Se, or the like) that acts nearly as an insulator to the charge having the same polarity as that of the charge applied to the first conductor layer and acts nearly as a conductor to the charge having the opposite polarity to that charge, a reading photoconducting layer (e.g., a material containing a-Se, Se—Te, Se—As—Te, metal-free phthalocyanine, metal phthalocyanine, MgPc, VoPc, CuPc, or the like) that exhibits photoconductivity on reception of electromagnetic waves for reading, and a second conductor layer having transmission to electromagnetic waves for reading. On the other hand, an electrostatic image reading apparatus for reading X-ray image information from the electrostatic recording sheet includes a scan and exposure unit that scans the electrostatic recording sheet while exposing the second conductor layer side of the sheet to electromagnetic waves for reading, and a current detecting unit for detecting current, which flows out from the electrostatic recording sheet by the scanning, via the first or second conductor layer.

Figure 13:
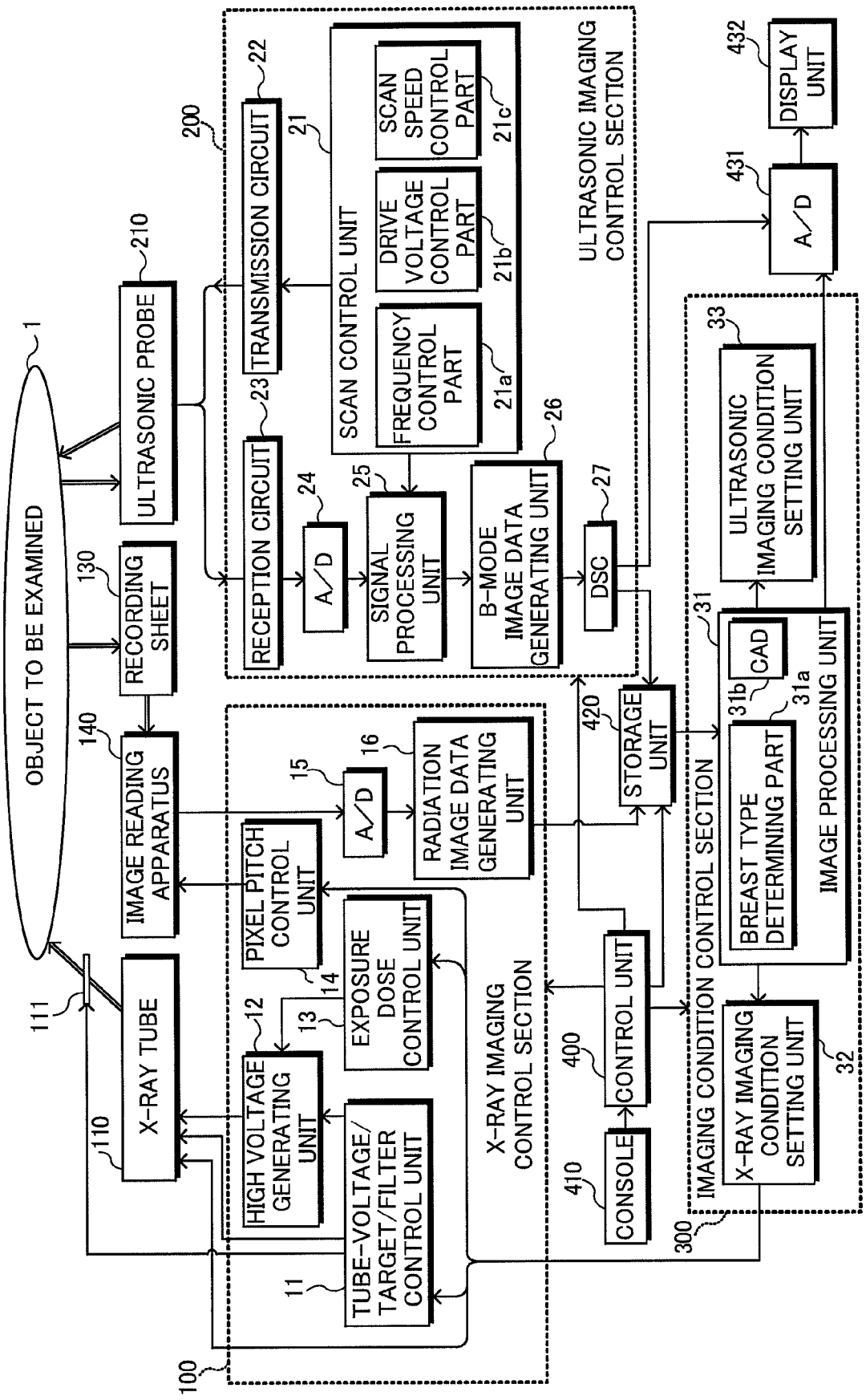
FIG. 13 is a block diagram showing a first modified example of the medical imaging system shown in FIG. 1.

When X-ray imaging is performed, the electrostatic recording sheet is provided in place of the X-ray detection unit 120 shown in FIG. 2, and the electrostatic image reading apparatus is provided in place of the image reading apparatus 140 shown in FIG. 13. When an X-ray is applied while a direct-current voltage is applied between the first conductor layer and the second conductor layer, X-ray image information is recorded on the electrostatic recording sheet. By inserting the electrostatic recording sheet into the electrostatic image reading apparatus, a detection signal representing the X-ray image information is outputted to the A/D converter 15.

In the above-mentioned medical imaging system and medical imaging method, two kinds of imaging technologies of X-ray mammography and ultrasonic imaging are combined.

Next, a medical imaging system according to the second embodiment of the present invention will be explained.

FIG. 14 is a block diagram showing a configuration of a medical imaging system according to the second embodiment of the present invention. As shown in FIG. 14, the medical imaging system includes plural kinds of imaging modalities (imaging apparatuses) 501-507 each for imaging an object to be inspected to generate a medical image, an imaging condition setting apparatus 510 for setting imaging condition in one imaging modality based on the medical image generated by another imaging modality, a medical image server 520 for storing medical image data, a plurality of medical image display apparatuses 531 and 532 for displaying medical images, an image interpretation report creating apparatus 540 to be used by an image interpretation doctor when creating an image interpretation report, an image interpretation report server 550 for storing image interpretation report data. Those apparatuses are connected to one another via a network such as a LAN (local area network). Further, the medical imaging system may be connected to RIS (radiology information system).

As imaging modalities, as well as a radiation mammography apparatus 501 and a US (ultrasonic diagnostic) apparatus 502, MRI (magnetic resonance imaging) apparatus 503, PET (positron emission tomography) apparatus 504, an imaging apparatus using near-infrared light 505, a breast fluorescence image acquiring apparatus 506, a fluorescent CT (computed tomography) apparatus 507, and so on are employed.

In the embodiment, plural known imaging technologies according to different imaging principles from each other are combined. In any combination of technologies, images more suitable for medical diagnoses can be efficiently generated by controlling imaging condition in one imaging technology based on medical images acquired by another imaging technology. Therefore, in medical diagnoses based on two or more kinds of medical images, quality and efficiency of diagnoses can be improved.

Here, the imaging apparatus using near-infrared light 505 will be explained. Near-infrared light has a nature to be absorbed more in a part with more blood. On the other hand, when a cancer is produced in the object, cells grow and capillary vessels increase. Accordingly, near-infrared light at plural wavelengths are applied to the breast, the concentration of hemoglobin is measured by measuring the amount of reflected light or transmitted light thereof, and thereby, a region where blood flow concentrates, that is, a region suspected to be a cancer can be detected (a reference book: Mamoru TAMURA, "Medical diagnosis using light", KYORITSU SHUPPAN, co., Ltd., pp. 38-44).

In the case where the imaging apparatus using near-infrared light 505 is combined with another imaging modality (ultrasonic diagnostic apparatus, CT apparatus, or the like), for example, when a lesion is detected in the other imaging modality, measurement of near-infrared light with high density is performed to acquire detailed images in the imaging apparatus 505, and, when no lesion is detected in the other imaging modality, measurement of near-infrared light with low density is performed for reduction of examination time in the imaging apparatus 505.

Next, the breast fluorescence image acquiring apparatus 506 will be explained. A breast fluorescence image is an image generated based on a detection result obtained by giving a fluorescence reagent having affinity to a tumor such as a cancer to an examinee in advance, applying excitation light to the breast of the examinee, detecting light intensity of fluorescence emitted from the breast. The breast fluorescence image acquiring apparatus 506 has a structure in which (i) a radiation source holding unit for holding a radiation source that emits radiation (e.g. X-ray) and an excitation light source that emits excitation light and (ii) an imaging stage on which the breast of the examinee is to be placed are connected by an arm in opposed positions, and further, the arm is mounted to a base.

In the case where the breast fluorescence image acquiring apparatus 506 is combined with another imaging modality (ultrasonic diagnostic apparatus, CT apparatus, or the like), for example, when a lesion is detected in the other imaging modality, the intensity of the excitation light is increased to perform detection with high S/N and/or detection with high density in the breast fluorescence image acquiring apparatus 506, and, when no lesion is detected in the other imaging modality, the intensity of the excitation light is not changed to perform detection with low density for reduction of examination time in the breast fluorescence image acquiring apparatus 506.

Further, the fluorescent CT apparatus 507 will be explained. Fluorescent CT is a technology of generating a fluorescent tomographic image by giving a fluorescence reagent to an examinee in advance, and obtaining a distribution of the amount of fluorescence in the breast of the examinee. The fluorescent CT apparatus 507 has a first light applying unit for applying a first extremely-short pulsed light to an object to be inspected, a second light applying unit for applying a second extremely-short pulsed light to the object, a photodetecting unit for detecting a spatial distribution and change of the amount of the first extremely-short pulsed light that has propagated within the object, an optical characteristic value distribution calculating unit for calculating an optical characteristic value distribution within the object based on a detection result of the photodetecting unit, a fluorescence detecting unit for detecting a spatial distribution and change of the amount of fluorescence that has been emitted from the object by application of the second extremely-short pulsed light and propagated within the object, a fluorescence distribution calculating unit for calculating a distribution of the amount of fluorescence radiation within the object based on a detection result of the fluorescence detecting unit and the optical characteristic value distribution that has been calculated by the optical characteristic value distribution calculating unit, and a tomographic image generating unit for generating a tomographic image of the object based on the distribution of the amount of fluorescence radiation calculated by the fluorescence distribution calculating unit.

In the case where the fluorescent CT apparatus 507 is combined with another imaging modality, for example, as is the case with the breast fluorescence image acquiring apparatus, when a lesion is detected in the other imaging modality, detection with high density and detailed image reconfiguration are performed in the fluorescent CT apparatus 507, and, when no lesion is detected in the other imaging modality, detection with low density is performed without changing the intensity of the excitation light for reduction of examination time and coarse reconfiguration is performed in the fluorescent CT apparatus 507.

The invention claimed is:

1. A medical imaging system comprising:
    a radiation mammography apparatus configured for applying radiation to a breast and generating a radiation image based on a detection signal obtained by detecting the radiation transmitted through the breast;
    an ultrasonic imaging apparatus configured for transmitting ultrasonic waves to the breast and generating an ultrasonic image based on a reception signal obtained by receiving ultrasonic echoes reflected within the breast;
    first means for determining a density of a mammary gland of the breast represented in the radiation image generated by said radiation mammography apparatus based on image data representing the radiation image; and
    second means for automatically setting an imaging condition in said ultrasonic imaging apparatus according to the density of a mammary gland of the breast determined by said first means, said imaging condition including at least one of output power of the ultrasonic waves and a scan speed of the ultrasonic waves for an object.

2. The medical imaging system according to claim 1, wherein said first means is configured to obtain a histogram of values of the image data representing the radiation image, and further configured to determine the density of the mammary gland of the breast represented in the radiation image based on a value at a barycenter of the histogram.

3. The medical imaging system according to claim 1, further comprising:
a compression plate configured for compressing the breast to make a thickness of the breast uniform at a time of imaging by said radiation mammography apparatus and a time of imaging by said ultrasonic imaging apparatus.

4. A medical imaging system comprising:
a radiation mammography apparatus configured for applying radiation to a breast and generating a radiation image based on a detection signal obtained by detecting the radiation transmitted through the breast;
an ultrasonic imaging apparatus configured for transmitting ultrasonic waves to the breast and generating an ultrasonic image based on a reception signal obtained by receiving ultrasonic echoes reflected within the breast;
first means for detecting a lesion part caused in the breast represented in the radiation image generated by said radiation mammography apparatus based on image data representing the radiation image; and
second means for automatically setting imaging condition in said ultrasonic imaging apparatus according to whether the lesion part is detected or not by said first means, said imaging condition including at least one of a transmission frequency of the ultrasonic waves, output power of the ultrasonic waves, and a scan speed of the ultrasonic waves for an object.

5. The medical imaging system according to claim 4, wherein said first means is configured to detect the lesion part by CAD (computer aided detection).

6. The medical imaging system according to claim 4, wherein said first means is configured to detect the lesion part caused in the breast represented in the radiation image based on at least one of (i) differential image data obtained by subtracting smoothed image data from the image data representing the radiation image, said smoothed image data being obtained by performing morphology processing on said image data, (ii) degree of concentration of gradient vectors obtained with respect to each pixel forming the radiation image, and (iii) correlation values obtained by matching outlines extracted from the radiation image with templates.

7. A method of generating medical images in a medical imaging system including a radiation mammography apparatus and an ultrasonic imaging apparatus, said method comprising the steps of:
(a) applying radiation to a breast and generating a radiation image based on a detection signal obtained by detecting the radiation transmitted through the breast by employing said radiation mammography apparatus;
(b) transmitting ultrasonic waves to the breast and generating an ultrasonic image based on a reception signal obtained by receiving ultrasonic echoes reflected within the breast by employing said ultrasonic imaging apparatus;
(c) determining, prior to step (b), density of a mammary gland of the breast represented in the radiation image generated at step (a) based on image data representing the radiation image; and
(d) automatically setting an imaging condition at step (b) according to the density of the mammary gland of the breast determined at step (c), said imaging condition including at least one of output power of the ultrasonic waves and a scan speed of the ultrasonic waves for an object in said ultrasonic imaging apparatus.

8. A method of generating medical images in a medical imaging system including a radiation mammography apparatus and an ultrasonic imaging apparatus, said method comprising the steps of:
(a) applying radiation to a breast and generating a radiation image based on a detection signal obtained by detecting the radiation transmitted through the breast by employing said radiation mammography apparatus;
(b) transmitting ultrasonic waves to the breast and generating an ultrasonic image based on a reception signal obtained by receiving ultrasonic echoes reflected within the breast by employing said ultrasonic imaging apparatus;
(c) detecting, prior to step (b), a lesion part caused in the breast represented in the radiation image generated at step (a) based on image data representing the radiation image; and
(d) automatically setting an imaging condition at step (b) according to whether the lesion part is detected or not at step (c), said imaging condition including at least one of a transmission frequency of the ultrasonic waves, output power of the ultrasonic waves, and a scan speed of the ultrasonic waves for an object in said ultrasonic imaging apparatus.

* * * * *